United States Patent
Gealon

(10) Patent No.: US 7,140,881 B1
(45) Date of Patent: Nov. 28, 2006

(54) PROTECTIVE THROAT SCREEN FOR DENTISTRY

(76) Inventor: Robyn Gealon, 2039 Pheasant Ct., Bend, OR (US) 97701

( * ) Notice: Subject to any disclaimer, the term of this patent is extended or adjusted under 35 U.S.C. 154(b) by 80 days.

(21) Appl. No.: 10/756,694

(22) Filed: Jan. 12, 2004

Related U.S. Application Data

(60) Provisional application No. 60/440,523, filed on Jan. 15, 2003.

(51) Int. Cl.
*A61C 5/14* (2006.01)
(52) U.S. Cl. .................................................. 433/136
(58) Field of Classification Search ............... 433/136, 433/137; 2/9; 128/850, 859
See application file for complete search history.

(56) References Cited

U.S. PATENT DOCUMENTS

| | | | |
|---|---|---|---|
| 1,774,285 A | | 4/1930 | Middaugh |
| 2,613,441 A | * | 10/1952 | Biggs ........................ 433/136 |
| 2,720,027 A | * | 10/1955 | Johnston .................... 433/136 |
| 2,937,445 A | | 5/1960 | Erickson |
| 3,772,790 A | | 11/1973 | Swn-Gett et al. |
| 4,259,067 A | | 3/1981 | Nelson |
| 4,471,771 A | * | 9/1984 | Steven et al. ............... 128/859 |
| 4,544,357 A | | 10/1985 | Williams |
| 4,828,491 A | | 5/1989 | Gray |
| 4,867,148 A | * | 9/1989 | Gomez ....................... 128/858 |
| 4,889,491 A | | 12/1989 | Krygier et al. |
| 5,931,673 A | | 8/1999 | Bolbolan |
| 2003/0031980 A1 | * | 2/2003 | Owais ......................... 433/136 |

* cited by examiner

*Primary Examiner*—Todd E. Manahan
(74) *Attorney, Agent, or Firm*—Laurence C. Bonar

(57) ABSTRACT

This invention provides a throat screen which can be placed in a dental patient's mouth during dental procedures, comprising a central porous area, with openings sufficiently numerous and of sufficient size to permit breathing through the mouth and draining of excess saliva into the throat, but small enough to prevent the passage into the throat of any debris produced during dental procedures, or small dental objects introduced into the dental patient's mouth during such dental procedures. The throat screen further comprising a rim which biases the screen against the inside of the mouth. The throat screen is preferably fabricated of plastic so as to make it economical to be disposable.

7 Claims, 1 Drawing Sheet

PROTECTIVE THROAT SCREEN FOR DENTISTRY

This application claims benefit of Provisional Application for Patent 60/440,523 filed Jan. 15, 2003

TECHNICAL FIELD OF THE INVENTION

This invention relates to a protective throat screen to enhance the safety of dental practice.

BACKGROUND

The practice of dentistry and dental or oral surgery frequently involves the production of small particles of debris in the patient's oral cavity, such as particles of dental amalgam or other restorative material, chips of teeth produced during extraction of a tooth or the drilling or other preparation of a tooth for restoration, or bits of debris removed from teeth during dental hygiene treatment. Furthermore, during dental procedures, small objects such as crowns, inlays, bridges, implants, etc. must often be introduced into the oral cavity. It is generally necessary that the dental patient be in an almost supine position, with the head back and the mouth opened wide, to allow the dental practitioner full access to the patients mouth and teeth. In this position, small particles produced in the oral cavity, or objects which fall or are accidentally dropped in the oral cavity may fall down the patient's throat and either be ingested into the esophagus or aspirated into the trachea.

Aspiration into the respiratory tract or lungs is particularly dangerous, since any foreign object carries with it the danger of infection and/or toxic or allergic reaction. Ingestion may also pose significant risk, since many of the products used in restorative dentistry may be toxic or allergenic in their uncured state, or as in the case of dental amalgam scrapings, present a long-term toxicity risk.

Dental practice regulations in most states require that a patient who has aspirated or swallowed a dropped crown, inlay, bridge, etc. undergo x-ray examination to determine where the object has lodged, and an ingested or inhaled dropped dental object may require follow-up medical care to insure against further medical problems.

Accidental ingestion or inhalation of dropped dental objects by a patient also adds significantly to the malpractice liability of the dental practitioner.

Furthermore, such objects as crowns, inlays and bridges cost hundreds of dollars to make, so that, even absent any harmful medical complications, accidental loss of these objects results in considerable economic loss to patient or dental practitioner and/or the distasteful task of recovering the object after it passes through the gastrointestinal tract.

For many dental procedures, dental dams, consisting of a thin sheet of latex rubber or similar material extending over the patient's mouth and clamped in a frame held against the patient's face, are used to prevent dental debris or objects from being swallowed or inhaled. Such dental dams are illustrated in Bolbolan, U.S. Pat. No. 5,931,673.

Typically, a hole or holes are cut or punched in the dental dam to permit one or more teeth to protrude through the dam, and a portion of the dam is inserted into the oral cavity and clamped around the teeth to be isolated. While such dams are effective in preventing ingestion or inhalation of dental debris or objects, and offer the added advantage of isolating teeth to be treated from the oral cavity, they are awkward and time-consuming to attach, confining to work in, and are poorly tolerated by many patients. The dams interfere with the patient's ability to breath through the mouth, which many patients feel the need of doing under the stress of a dental procedure, and makes it difficult to swallow. As a result, such dams can produce sensations of claustrophobia or choking in many patients. Such dental dams are generally used only for procedures requiring isolating one or more teeth from the oral cavity.

Intraoral dental dams to avoid some of the difficulties in the use of conventional dental dams are taught inter alia by Swan-Gett et al, U.S. Pat. No. 3,772,790; by Gray, U.S. Pat. No. 4,828,491; and by Bolbolan, U.S. Pat. No. 5,931,673. The dams taught in these patents would appear to be effective in preventing ingestion or inhalation of dental debris or objects, but would not allow breathing through the mouth. The aforementioned dams would also prevent excess saliva from draining from the mouth into the throat, where it could be swallowed.

Krygier et al, U.S. Pat. No. 4,889,491, teaches the use of a perforated throat shield held at the opening of the throat by a support member. The throat shield of Krygier et al is designed to prevent ingestion or inhalation of dental debris or objects while allowing the patient to breathe through the mouth, and also allows excess saliva to drain from the mouth to the throat. The throat shield of Krygier et al is complex, and would be relatively expensive to produce as a disposable device.

Neither the throat shield of Krygier et al nor the intraoral dental dams of Swan-Gett et al, Gray, or Bolbolan have found any substantial acceptance among dental practitioners, and neither the throat shield of Krygier et al nor any of the intraoral dams described appear to be commercially available.

In current dental practice, careful practitioners use common 2" by 2" gauze squares, partially unfolded to 4" by 4", placed in the back of the mouth to prevent ingestion or inhalation of dental debris or objects. These gauze squares allow the patient to breathe through the mouth, and allow excess saliva to drain into the throat. However, they quickly get wet with saliva, leading to collapse and lack of coverage of the throat, so they must be replaced frequently during dental procedures.

There is a need for a simple device which will prevent the ingestion or inhalation of dental debris or objects while allowing the patient to breathe freely through the mouth, and which will allow excess saliva to drain into the throat where it may be swallowed as often as the patient wishes. The device should be inexpensive, so that it may be disposable, to avoid the necessity for sterilization after use or the risk of transmitting disease.

The present invention provides such a device.

OBJECTIVES AND SUMMARY OF THE INVENTION

It is an objective of the present invention to provide a throat screen for dental practice.

It is another objective of the present invention to provide such a throat screen which allows the dental patient to breathe freely through the mouth, and which allows excess saliva to flow from the oral cavity into the throat.

It is a further objective of the present invention to provide such a throat screen which is comfortable and well-tolerated by the dental patient.

It is a further objective of the present invention to provide such a throat screen which is easy for the dental practitioner to place in the dental patient's mouth, and which does not interfere with dental procedures.

It is a still further objective of the present invention to provide such a throat screen which is inexpensive to produce and hence disposable after use in a patient.

To accomplish these objectives, the throat screen of the present invention comprises a porous membrane or sheet shaped to fit snugly against the inside of the mouth when bent. The openings in the porous membrane or sheet are sufficiently large as not to impede breathing or the flow of saliva, but small enough to prevent dental debris or objects from passing through.

DETAILED DESCRIPTION OF THE INVENTION

The throat screen of the present invention comprises a central porous area, with openings sufficiently numerous and of sufficient size to permit breathing through the mouth, and draining of excess saliva into the throat, but small enough to prevent the passage into the throat of any debris produced in dental procedures or small dental objects which must be introduced into the mouth during such procedures. The throat screen of the present invention also comprises a solid or non-porous rim which can seal against the inside of the mouth when gently pressed against it. The throat screen of the present invention will be sufficiently flexible that it can be deformed to be inserted into a dental patient's mouth, but possess sufficient stiffness that it will partially unflex when the deforming force is relaxed, to press gently against the inside of the back of the mouth and thus hold the throat screen in place. The throat screen of the present invention comprises an upper portion which, in the partially flexed condition inside a dental patient's mouth, contacts and rests against the roof of a dental patient's mouth, a lower portion which, in the partially flexed condition inside a dental patient's mouth, contacts and rests against the floor of the patient's mouth, and lateral portions which, in the partially flexed condition inside a dental patient's mouth, contact and rest against the inside of the patient's cheeks. The throat screen of the present invention will thus prevent any solid material from entering the throat.

Figures 1, 2:
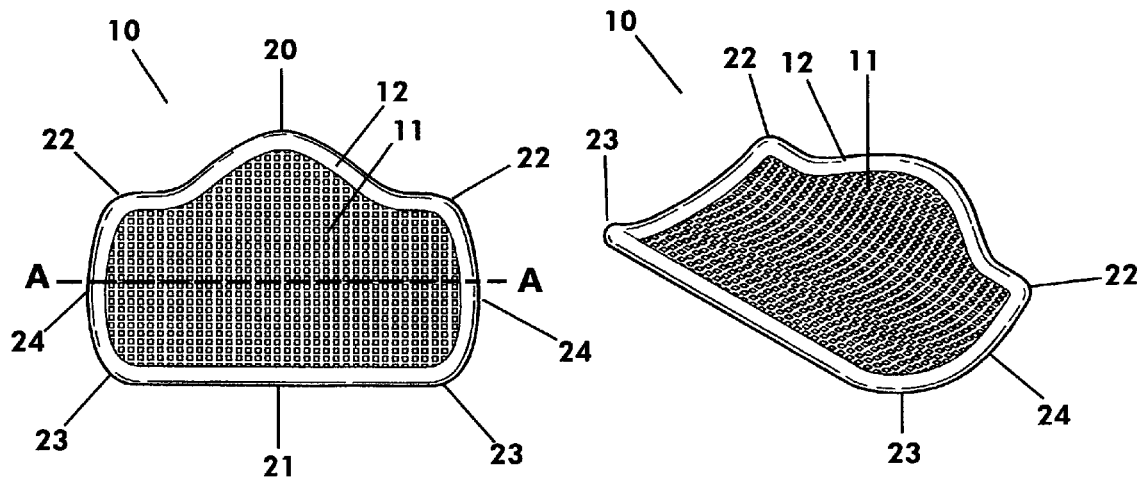
FIG. 1 is a front view of the preferred embodiment of the throat screen of the present invention in the flat, unconstrained configuration.
FIG. 2 is a perspective sketch of the preferred embodiment of the throat screen of the present invention in the flexed or bowed configuration as it would be in a patient's mouth.
Figure 3A:
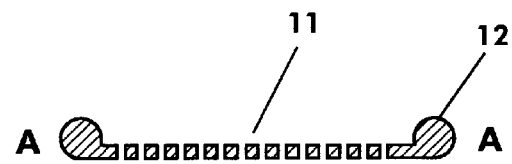
FIGS. 3a and 3b show cross sections at locus A—A of FIG. 1 for the preferred embodiment of the throat screen of the present invention and an alternate embodiment, respectively.

In preferred embodiments, as shown in FIGS. 1 2, and 3a and b, the throat screen of the present invention 10 comprises central area 11 which is perforated or consists of mesh, and outer rim 12, which will not be perforated. Throat screen 10 has an upper edge 20 and a lower edge 21, upper lateral corners 22 and lower lateral corners 23, and lateral edges 24. Throat screen 10 may be comprised of plastic, metal, stiff cloth, or any material with suitable flexibility and stiffness or resistance to flexing, and which can be produced in a substantially hygienic condition suitable for insertion into the mouth. Preferably, screen 10 will be comprised of plastic, most preferably polypropylene.

In the most preferred embodiment, central area 11 of screen 10 is polypropylene mesh obtainable from Sultan Dental Products of Englewood, N.J., or polyester netting obtainable from American Home & Habitat Inc., of King George, Va. Rim 12 is also preferably polypropylene, and can be produced by injection molding or other plastic fabrication techniques well known in the art. To fabricate this most preferred embodiment of throat screen 10, the mesh area is die-cut to the proper size, and rim 12 is then attached to the mesh by heat sealing, ultrasonic welding, or other attachment techniques well known in the art.

Cross-section A—A of this most preferred embodiment is shown in FIG. 3a.

Outer rim 12 will preferably be approximately circular in cross-section, and may be between about 1 mm. and 10 mm. in diameter, preferably between about 2 mm. and about 5 mm. in diameter. Central area 11 will be between 0.1 mm. and 10 mm. thick, and will preferably be between 0.2 mm. and 0.5 mm. thick The openings of the perforations or mesh in central area 11 will be sufficiently large to permit breathing through the mouth but small enough to catch any debris produced in dental procedures or small dental objects which must be introduced into the mouth during such procedures. Such openings may be between about 0.5 mm. and about 5 mm. across, and will preferably be about 1 mm. to about 2 mm. across.

The throat screen of the present invention will be flexible enough to allow flexing during placement in the oral cavity of the patient under dental treatment, but posses sufficient stiffness or resiliency that it will tend to unflex and conform sufficiently closely to the oral cavity of the patient under dental treatment that dental-debris or dental objects cannot bypass the throat screen. The throat screen will not, however, be so stiff as to press against the oral cavity with enough force to cause pain or discomfort to the patient.

In the most preferred embodiment of the throat screen of the present invention, the stiffness and resiliency will reside in rim 12.

The degree of flexibility and stiffness required to allow flexing during placement and unflexing to seal against the inside off the oral cavity can readily be determined by one skilled in the art without undue experimentation.

To use the throat screen of the present invention, throat screen 10 is inserted into the patient's wide-open mouth in a substantially unflexed state, lower edge first, then flexed and put into place, and allowed to unflex until it is constrained by the inside of the patient's mouth. The patient may then close his/her mouth slightly, to further flex throat screen 10 slightly. In its installed, partially flexed configuration, upper edge 20 of throat screen 10 will press gently against the patient's palate, at the back of the mouth, and upper lateral corners 22 formed when throat screen 10 is flexed. will rest against the tuberosity, on the roof of the mouth. Lower lateral corners 23 will contact the retromolar pads behind the lower teeth, and lower edge 21 will rest against the tongue. Lateral edges 24 will rest against the inside of the patient's cheeks. The dental screen of the present invention will thus close off and protect the patient's throat, while allowing breathing through the mouth and drainage of saliva, while dental practitioner can perform the dental procedures without fear of dropping debris or small objects into the patient's throat.

The throat screen of the present invention may be made in a plurality of different, graduated, sizes, to fit properly in the mouths of dental patients of different sizes.

In an alternate embodiment of the present invention, throat screen 10 may comprise a single piece of polypropylene or other material fabricated by die-cutting, injection molding or other techniques known to the art into the appropriate shape and perforated. The material would be of sufficient thickness to have the flexibility and stiffness needed to press gently against the inside of the back of the mouth of a dental patient and thus hold the throat screen in place. In this embodiment. rim 12 may be the same thickness as central area 11, or thicker. In such alternate embodiments, the thickness of central area 11 may be between 0.25 mm. and 5 mm., and the thickness of rim 12 may be between 1 mm. and 10 mm.

Figure 3B:
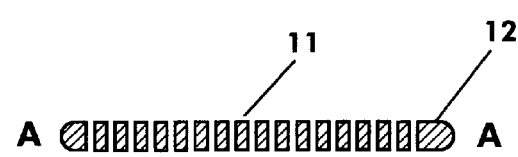

Cross-section A—A of this alternate embodiment is shown in FIG. 3b.

In another alternate embodiment, the throat screen of the present invention may comprise rim 12 which is thicker than central area 11 of throat screen 10, which rim may be formed, for example, by rolling an outer unperforated portion of the material comprising perforated central area 11, or by other fabrication techniques well known in the art. In this embodiment, central porous area 11 may be made thinner than in the uniform-thickness preferred embodiment, with the thickened rim providing the stiffness needed to partially unflex throat screen 10 so that the screen presses gently against the inside of the mouth.

In still another alternate embodiment, central area 11 may be comprised of non-woven fabric, of a porosity and surface treatment chosen to allow the passage of saliva and air, but block the passage of dental debris or small objects. One skilled in the art can readily select a suitable non-woven fabric without undue experimentation.

Other embodiments will be apparent to one skilled in the art, which will change various details of the present invention without limiting its scope. Furthermore, the foregoing description of the preferred embodiment of the invention and the best mode for practicing the invention are provided for the purpose of illustration only and not for the purpose of limitation of the invention, which will be defined by the claims.

The invention claimed is:

1. A throat screen containable within the oral cavity of a patient undergoing dental treatment, comprising a central porous section and a continuous resilient rim completely surrounding the periphery of said central porous section, said throat screen being bowed shaped and made of a material which is shape-retaining and soft and flexible so as to conform to the oral cavity and cover the throat of the dental patient, and resilient so as to press against the oral cavity of a dental patient.

2. The throat screen of claim 1 wherein the central porous portion is comprised of mesh.

3. The throat screen of claim 1 wherein the central porous portion is perforated.

4. The throat screen of claim 1 wherein the central porous portion is comprised of non-woven fabric.

5. The throat screen of claim 1 wherein said central porous section will allow the patient to breathe through the mouth and allow passage of saliva into the throat and prevent objects from passing into the patient's posterior throat area, esophagus and trachea.

6. The throat screen of claim 1 wherein said throat screen is insertable in a dental patient's oral cavity in a flexed condition and is capable of unflexing so as to press against the oral cavity of a dental patient.

7. A method for preventing small objects from passing into the throat, esophagus or trachea of a patient undergoing dental treatment, comprising the steps of:

flexing a throat screen, said throat screen containable within the oral cavity of a patient undergoing dental treatment and comprising a central porous section and a continuous resilient rim completely surrounding the periphery of said central porous section, said throat screen being bowed shaped and made of a material which is shape-retaining and soft and flexible so as to conform to the oral cavity and cover the throat of the dental patient, and resilient so as to press against the oral cavity of a dental patient;

inserting said flexed throat screen into the dental patient's oral cavity;

permitting said throat screen to unflex until constrained by the dental patient's oral cavity.

* * * * *